United States Patent [19]

New

[11] Patent Number: 4,880,930
[45] Date of Patent: Nov. 14, 1989

[54] PSYCHOTROPIC ACYCLIC AMIDE DERIVATIVES

[76] Inventor: James S. New, 168 Bradley Corners, Madison, Conn. 06483

[21] Appl. No.: 126,819

[22] Filed: Nov. 30, 1987

[51] Int. Cl.$^4$ .................. C07D 403/04; C07D 413/04; C07D 417/04
[52] U.S. Cl. .................................. 544/295; 544/362; 544/368
[58] Field of Search ........................ 544/293, 362, 368

[56] References Cited

U.S. PATENT DOCUMENTS

| | | | |
|---|---|---|---|
| 3,717,634 | 2/1973 | Wu et al. | 544/362 |
| 4,361,565 | 11/1982 | Temple et al. | 544/362 |
| 4,367,335 | 6/1983 | Temple et al. | 544/362 |
| 4,411,901 | 10/1983 | Temple et al. | 544/362 |
| 4,423,049 | 12/1983 | Temple | 544/362 |
| 4,524,206 | 6/1985 | New et al. | 544/362 |
| 4,619,930 | 10/1986 | New et al. | 544/362 |
| 4,668,687 | 5/1987 | Yevich et al. | 544/362 |
| 4,677,104 | 6/1987 | New et al. | 544/362 |

*Primary Examiner*—John M. Ford
*Attorney, Agent, or Firm*—Richard P. Ryan

[57] ABSTRACT

A series of psychotropic acyclic amide derivatives having the structure

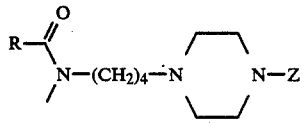

wherein R is alkyl, alkenyl, cycloalkyl- and bicycloalkyl-methyl; and Z is a heterocyclic group comprised of pyrimidine, benzisothiazole, thienopyridine, and furopyridine. These compounds are useful antipsychotic and/or anxiolytic agents.

26 Claims, No Drawings

PSYCHOTROPIC ACYCLIC AMIDE DERIVATIVES

BACKGROUND OF THE INVENTION

This invention generally pertains to heterocyclic carbon compounds having drug and bio-affecting properties and to their preparation and use. In particular, the invention is converned with 1,4-disubstituted piperazine derivatives wherein one substituent is an acyclic amide group attached at its nitrogen atom via a butylene chain and the other substituent is a heterocycle comprising pyrimidine, 1,2-benzisothiazole, thieno[3,2-c]pyridine, or furo[3,2-c]pyridine.

Related art may be viewed in terms of the following general structural formula 1

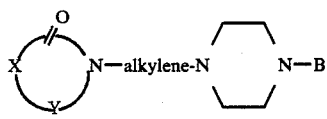

in which X is an optimally substituted $C_{2-3}$ alkylene fragment which taken with Y gives rise to a five or six membered ring; X may also contain a heteroatom such as oxygen or sulfur thereby forming a morpholine, thiazolidine, or related ring; X may also be a 1,2-benzo ring. In structure 1, Y is a carbonyl or methylene and B represents heteroaromatic systems with optional substituents. These and related compounds have been disclosed as psychotropic agents and are described in the following references.

Compounds of general structure 1 wherein X and Y are selected so that a cyclic imide such as glutarimide, succinimide, phthalimide,, and the like is formed have been disclosed and claimed in the following representative patent references.

Wu, et al., in U.S. Pat. No. 3,717,634; Temple, et al., in U.S. Pat. No. 4,361,565 and U.S. Pat. No. 4,411,901; and Temple, in U.S. Pat. No. 4,423,049 disclose and claim compounds of formula 2

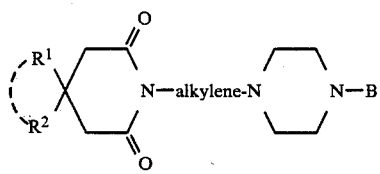

wherein $R^1$ and $R^2$ are alkyl groups or are joined to form $C_4$ or $C_5$ alkylene bridges and B can be a substituted or unsubstituted pyridine, pyrimidine, or benzisothiazole ring.

Succinimide ring examples (formula 3) are described in New, et al., U.S. Pat. No. 4,524,206.

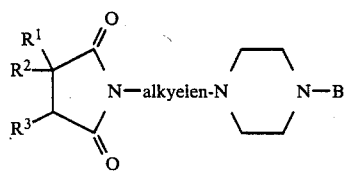

Other hetero atom containing cyclic imide rings such as morpholinediones, thiazolodinediones, and the like have been described in references represented by Temple, et al., U.S. Pat. No. 4,411,901 and U.S. Pat. No. 4,367,335 and by New, et al., in U.S. Pat. No. 4,619,930.

Examples of psychotropic compounds wherein B is a fused heterocyclic ring structure comprising thieno[3,2-c]pyridine, and furo[3,2-c]pyridine were disclosed and claimed by New, et al., in U.S. Pat. No. 4,677,104.

Finally pyrimidinylpiperazinyl derivatives of pyrrolidinones (Y=CH₂) have been disclosed by Yevich, et al., in U.S. Pat. No. 4,668,687 as being cognition and memory enhancing agents.

None of these aforementioned references disclose or suggest the psychotropic compounds of the instant invention whose structures comprise acyclic amide moieties.

SUMMARY OF THE INVENTION

This invention concerns a new series of CNS-active compounds characterized by the following general structural formula I

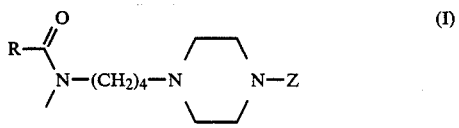

and the pharmaceutically acceptable acid addition salts thereof. In the foregoing formula, R is $C_{4-8}$ alkyl, alkenyl, cycloalkylmethyl, and $C_{8-9}$ bicycloalkylmethyl and bicycloalkylenemethyl. These alkyl, alkenyl and cycloalkylmethyl groups contain from four to eight carbon atoms and can be branched as well as straight chain hydrocarbon moieties as their structures permit. The $C_{8-9}$ bicyclo hydrocarbon moieties have the formula

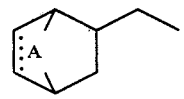

wherein A is methylene or ethylene and the full line accompanying the dotted line is a single or double covalent bond. The letter Z, of formula I, denotes a heterocyclic ring system which is selected from the group: pyrimidine, 1,2-benzisothiazole, thieno[3,2-c]pyridine and furo[3,2-c]pyridine. The compounds of formula I are psychotropic agents possessing anxiolytic and/or antipsychotic properties.

DETAILED DESCRIPTION OF THE INVENTION

The compounds comprising this invention correspond in structure to formula I, shown and described hereinabove. Contemplated classes of compounds are distinguished by their therapeutic classification. Class 1 is comprised of the compounds of formula I wherein Z is the anxiolytic predisposing pyrimidine ring and Class 2 is comprised of formula I compounds wherein Z is the antipsychotic predisposing 1,2-benzisothiazole, thieno[3,2-c]pyridine, and furo[3,2-c]pyridine rings.

For both classes of compounds, R can be an alkyl or alkenyl group containing from 4 to 8 carbon atoms arranged in straight chain or branched configurations. R is also intended as cycloalkylmethyl groups containing from 4 to 8 carbon atoms and would be comprised of groupings from cyclopropylmethyl to cycloheptylmethyl. Finally, R is intended as $C_{8-9}$ bicycloalkylmethyl and bicycloalkenylmethyl groups which may be represented as the following formula

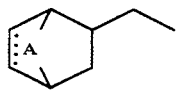

in which A is a methylene or ethylene group and the full line accompanying a broken line ( ) indicates a single bond or a double bond.

Selected compounds exemplary of these hereinabove-described structural variations display useful psychotropic properties comprising antianxiety and/or antipsychotic action.

It is to be understood that, as used herein, the compounds comprising one aspect of this invention are intended to encompass pharmaceutically acceptable acid addition salts and solvates as well as the base form of these compounds.

Pharmaceutically acceptable acid addition salts of the invention are those in which the anion does not contribute significantly to the toxicity or pharmacological activity of the salt and, as such they are the pharmacological equivalents of the bases of Formula I. These are generally preferred for medical usage. In some instances, these have physical properties which make them more desirable for pharmaceutical formulation such as solubility, lack of hygroscopicity, compressibility with respect to tablet formation and compatibility with other ingredients with which the substances may be used for pharmaceutical purposes. The salts are routinely made by mixture of the Formula I base with the selected acid preferably by contact in solution employing an excess of commonly used inert solvents such as water, ether, benzene, alcohol, e.g. ethanol, ethyl acetate, acetonitrile, and so forth. The salts may also be made by methathesis or treatment with an ion exchange resin under conditions in which the anion of one salt of the substance of the Formula I is replaced by another anion under conditions which allow for separation of the desired species such as by precipitation from solution or extraction into a solvent, or elution or retention on an ion exchange resin. Examples of pharmaceutically acceptable acids for the purposes of salt formation of the substances of Formula I comprise sulfuric, phosphoric, hydrochloric, hydrobromic, hydroiodic, citric, acetic, benzoic, cinnamic, mandelic, nitric, mucic, isethionic, palmitic, heptanoic, and others.

The compounds of Formula I are prepared by means of a three step reaction sequence depicted in Scheme 1.

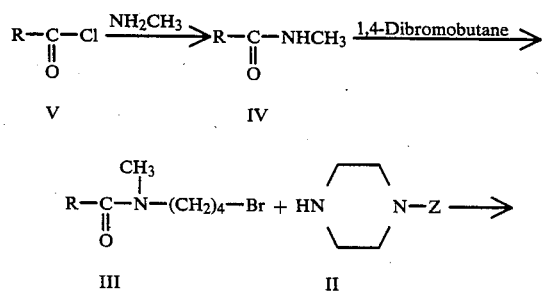

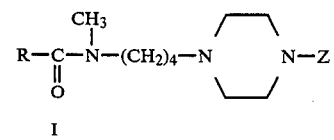

I

Reaction of acid chloride compounds of Formula V with methylamine provided the N-methyl amides of Formula IV. The acid chlorides (V) are either commercially available or they may be readily obtained by chlorination of the appropriate carboxylic acid in a manner which would be understood by one skilled in the art of synthetic organic chemistry. Alkylation of the N-methyl amides (IV) with 1,4-dibromobutane produced the intermediate bromo-amide compound of Formula III. These intermediate III compounds are subsequently reacted with a variety of heteroaryl piperazines of Formula II to yield the desired products of Formula I.

The synthetic steps comprising the process of Scheme 1 are well known to those skilled in organic chemistry and the details are readily available in the chemical literature. This process may be adapted to variation in order to produce other compounds embraced by this invention but not specifically disclosed. Variations of the methods to produce the same compounds in somewhat different fashion will also be evident to one skilled in the art. Certain examples will be given for specific illustration.

The heteroaryl piperazines of Formula II are described in the aforementioned Wu, et al., Temple, et al. and New, et al. patents and certain references cited therein. These procedures are applicable to the preparation of all the heteroarylpiperazines required as intermediates for the process of scheme 1.

The compounds of the instant invention are useful pharmacological agents with psychotropic properties. In this regard, they exhibit activity at non-toxic doses as anxiolytic and/or antipsychotic agents. Compounds of Formula I wherein Z is a 2-pyrimidinyl moiety are also active in reversing catalepsy. The following in vivo screening tests were utilized as the basis to determine the pharmacological profile of the instant compounds.

| Behavioral Test | Reference |
|---|---|
| Suppression of Conditioned Avoidance Response (CAR) | Albert, Pharmacologist, 4, 152 (1962); Wu, et al., J. Med. Chem., 12, 876–881 (1969) |
| Reversal of trifluoperazine-induced catalepsy | Berkson, Amer. Statist. Assoc., 48: 565–599 (1953). |
| Blockade of apomorphine-induced stereotyped behavior | Janssen, et al., Arzneimittel-Forsch, 17: 841 (1966). |

The CAR test is generally considered to be a measure of the anxiolytic and/or antipsychotic potential iof a drug. It is determined by assaying the drug's ability to attenuate an avoidance response to an electrical shock in trained, fasted rats. The reversal of neuroleptic-induced catalepsy in the rat is considered a desirable component in a compound's biological profile because it may be predictive of a low propensity to induce extrapyramidal side effects in man. The blockade of apomorphine-induced stereotyped behavior in rats may reflect dopamine antagonist activity and is a fairly specific screen for antipsychotic activity.

Activity in the CAR test with little effect on apomorphine-induced stereotyped behavior in rats can be taken as being predictive of anxiolytic potential. To aid in subclassification of the psychotropic activity and specificity of the instant compounds, state of the art in vitro central nervous system receptor binding methodology is employed. Binding affinity for 5-HT$_{1A}$ receptor sites is suggestive of anxiolytic activity, cf: Dourish, et al., *Trends in Pharmacological Science*, 212–214, (1986); Bockaert, et al., *Naunyn-Schmiedeberg's Arch. Pharmacol.* 658: 1–5 (1987). Compounds in which Z is pyrimidine exhibited binding at the 5-HT$_{1A}$ site. Selected representative compounds from this subclass also exhibited in vivo activity in a modified Vogel conflict test which is a procedure for testing antianxiety compounds, cf: Vogel, et al., *Psychopharmacologia* (Berl.) 21, 1–7 (1971).

According to the pharmacological profile established by the aforementioned tests, representative compounds of Formula I have promising tranquilizing potential, either antianxiety and/or antipsychotic activity, in that they are relatively potent in the CAR test, having oral ED$_{50}$ values <100 mg/kg body weight. Concerning prediction of side-effect liability, certain Formula I compounds wherein Z is a pyrimidine ring show activity in the reversal of trifluoperazine-induced catalepsy test by virtue of ED$_{50}$ values being <20 mg/kg, p.o. Activity in this test suggests that the compounds lack the potential for eliciting the unwanted side effects associated with extrapyramidal symptomatology.

The pharmacological profiles established by the above-described tests also served to classify the Formula I compound as either anxiolytic or antipsychotic agents. Activity in the CAR and in blockade of apomorphine-induced stereotyped behavior is predictive of antipsychotic activity. Compounds having ED$_{50}$ values <100 mg/kg body weight in these tests are psychotropics with antipsychotic properties. Formula I compounds, active in the CAR test, but not active in the apomorphine test are classified as anxiolytics on the basis of 5-HT$_{1A}$ binding and Vogel conflict test results. On these bases the Formula I compounds wherein Z is pyrimidine were classed as psychotropics with anxiolytic properties and a low side-effect potential and the Formula I compounds wherein Z is 1,2-benzisothiazole,thieno-[3,2-c]pyridine and furo[3,2-c]pyridine are psychotropics with antipsychotic properties.

Another aspect of the instant invention provides a method for treating a mammal afflicted with anxiety or psychosis which comprises administering systemically to said mammal a therapeutically effective amount of a compound of Formula I or a pharmaceutically acceptable acid addition salt thereof.

The administration and dosage regimen of compounds of Formula I is considered to be done in the same manner as for the reference compound clozapine, cf: *The Merck Index*, 10th Edition, (1983), page 344, and references therein. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferably, 0.1 to 2 mg/kg, when administered parenterally; and from about 1 to about 50 mg/kg, preferably 2 to 30 mg/kg, when administered orally. In some instances, a sufficient therapeutic effect can be obtained at lower doses while in others, larger doses will be required. Systemic administration refers to oral, rectal and parenteral (i.e. intramuscular, intravenous and subcutaneous). Generally, it will be found that when a compound of the present invention is administered orally, a larger quantity of the active agent is required to produce the same effect as a similar quantity given parenterally. In accordance with good clinical practice, it is preferred to administer the instant compounds at a concentration level that will produce effective anxiolytic effects without causing any harmful or untoward side effects.

The compounds of the present invention may be administered for anxiolytic purposes either as individual therapeutic agents or as mixtures with other therapeutic agents. Therapeutically, they are generally given as pharmaceutical compositions comprised of a tranquilizing amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or orally suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch); and wetting agents (e.g. sodium lauryl sulfate)1. Solutions or suspensions of a Formula I compound with conventional pharmaceutical vehicles are employed for parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not be construed as limiting the invention in sphere or scope. In the following examples, used to illustrate the foregoing synthetic processes, temperatures are expressed in degrees Celsius and melting points are uncorrected. The nuclear magnetic resonances (NMR) spectral characteristics refer to chemical shifts ($\delta$) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad singlet (bs), singlet (s), multiplet (m) or doublet (d). Abbreviations employed are DMSO-d$_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

The following examples describe in detail the preparation of compounds of formulas I, III and IV. It will be apparent to those skilled in the art that modifications, both of materials and methods, will allow preparation of other compounds disclosed herein. From the foregoing description and the following examples it is believed that one skilled in the art is able to use the invention to the fullest extent.

A. PREPARATION OF FORMULA IV COMPOUNDS

TYPICAL PREPARATION OF FORMULA IV COMPOUNDS

Example 1

N,3-Dimethylbutanamide (IV-1)

A seven fold excess solution of 40% aqueous methylamine stirring at 10° C. was treated dropwise with a solution of isovaleryl chloride (V) (38.1 g, 0.3 mol) in ether. The mixture was vigorously stirred 15 min. beyond the conclusion of this addition, the organic layer was isolated, dried (MgSO$_4$), filtered, and concentrated in vacuo yielding 32 g (84%) of a yellow oil whose spectroscopic data was consistent with the assigned structure.

All acid chlorides used in this reaction, if not commercially available, were readily obtained from the carboxylic acid precursors. The acylation products were generally used without additional purification, but occasionally kugelrohr distillation was employed to effect their isolation. Table 1 presents yields of analogous products which were used as precursors in the preparation of intermediates of Formula III.

TABLE 1

Preparation of Formula IV Compounds $$R-\overset{O}{\underset{\|}{C}}-NH-CH_3 \qquad IV$$

| Example No. | R | % Yield |
|---|---|---|
| 1 | (H$_3$C)$_2$CH—CH$_2$— | 84 |
| 2 | CH$_3$CH$_2$CH(CH$_3$)— | 95 |
| 3 | cyclopentyl | 99 |
| 4 | (H$_3$C)$_3$C—CH$_2$— | 77 |
| 5 | cyclohexyl-CH$_2$— | 95 |
| 6 | norbornyl-CH$_2$— | 96 |
| 7 | (H$_3$CCH$_2$)$_2$CH— | 74 |
| 8 | (nPr)$_2$CH— | 89 |
| 9 | Et—CH=CH—CH$_2$— | 100 |
| 10 | H$_3$C—CH$_2$—CH(CH$_3$)—CH$_2$— | 60 |
| 11 | (H$_3$C)$_2$C=CH— | 98 |

B. PREPARATION OF FORMULA III COMPOUNDS

TYPICAL PREPARATION OF FORMULA III COMPOUNDS

Example 12

N-(4-Bromobutyl)-N,3-dimethylbutanamide III-12)

A mixture of 10 g (0.086 mol) of 1, 56 g (0.26 mol) of 1,4-dibromobutane, and 5.2 g (0.22 mol) of 94% sodium hydride was refluxed overnight in tetrahydrofuran (400 ml). Upon completion of the reaction, the mixture was partitioned between chloroform and water. The organic phase was isolated, dried (MgSO$_4$), and concentrated in vacuo. High vacuum distillation (Kugelrohr) was used to remove the excess 1,4-dibromobutane and, when desirable, to distill the product. The isolation 12.4 g (57%) of amide product III (R=(CH$_3$)$_2$CHCH$_2$—) rendered a product of sufficient purity to be used in the next reaction step without additional purification. Table 2 presents yields of other Formula III products obtained in a similar manner.

TABLE 2

Preparation of Formula III Compounds $$R-\overset{O}{\underset{\|}{C}}-\underset{\underset{CH_3}{|}}{N}-(CH_2)_4-Br \qquad III$$

| Compound No. | R | % Yield |
|---|---|---|
| 12 | (H$_3$C)$_2$CH—CH$_2$— | 57 |
| 13 | (H$_3$C)$_3$C—CH$_2$— | 20 |
| 14 | CH$_3$CH$_2$CH(CH$_3$)— | 29 |
| 15 | cyclopentyl | 30 |
| 16 | cyclohexyl-CH$_2$— | — |
| 17 | norbornyl-CH$_2$— | 78 |
| 18 | (H$_3$CCH$_2$)$_2$CH— | 25 |
| 19 | (nPr)$_2$CH— | 54 |
| 20 | Et—CH=CH—CH$_2$— | 75 |

TABLE 2-continued

Preparation of Formula III Compounds $$R-\underset{\underset{O}{\|}}{C}-\underset{\underset{CH_3}{|}}{N}-(CH_2)_4-Br \qquad III$$

| Compound No. | R | % Yield |
|---|---|---|
| 21 | H₃C—CH₂—CH(CH₃)—CH₂— | 53 |
| 22 | (H₃C)₂C=CH— | 75 |

C. PREPARATION OF FORMULA I COMPOUNDS

The heteroarylpiperazines of Formula II are prepared by the methods detailed in U.S. Pat. No. 3,717,634; U.S. Pat. No. 4,411,901; and U.S. Pat. No. 4,677,104; all of which are hereby imcorporated by reference into the disclosure contained in this specification. These Formula II compounds are required in the synthesis of the Formula I CNS agents as shown in the following.

TYPICAL PREPARATION OF FORMULA I COMPOUNDS

Example 23

N,3-Dimethyl-N-[4-[4-(1,2-benzisothiazol-3-yl)-1-piperazinyl]butyl]-butanamide dihydrochloride (I-23)

A mixture of 3.5 g (0.014 mol) of III-12, 3.1 g (0.014 mol of 3-(1-piperazinyl)-1,2-benzisothiazole (II), and 5.8 g (0.042 mol) of potassium carbonate was refluxed 48 hrs. in acetonitrile (200 ml), filtered, and concentrated in vacuo. The crude mixture was flash chromatographed (4% ethanol-chloroform), and 2.9 g (54%) of a light colored oil product was recovered. The oil was dissolved in ethanol, treated with 2 equivalents of ethanolic hydrochloric acid, and crystallized from a 1:1 mixture of ethanol-ethyl acetate to yield 3.5 g (54%) of material, mp 144°–145°.

Elemental analysis (C, H, and N) agreed with $C_{21}H_{32}N_4OS \cdot 2HCl$.

Spectral analysis:

IR(KBr) 3450, 2950, 2870, 2450, 1655, 1635, 1590, 1500, 1430, 1420, 1380, 1275, 860, 775, 745 cm$^{-1}$; $^1$H NMR (Me₂SO-d₆) δ-0.93 (d, J=6.0 Hz, 6H), 1.68 (m, 5H), 2.20 (m, 2H), 2.86 (s), 2.99 (s, 3H), 3.35 (m, 10H), 4.11 (m, 2H), 7.56 (m, 2H), 8.16 (m, 2H),, 10.50 (br s, 2H),, 11.80 (br s, 1H), ppm; $^{13}$C NMR (Me₂SO-d₆) 20.3, 22.4, 24.0, 24.9, 33.0, 35.1, 38.3, 41.3, 46.2, 50.4, 55.2, 121.1, 124.0, 124.5, 126.9, 128.0, 152.1, 162.2, 171.2, 171.3 ppm. Both the $^1$H and $^{13}$C NMR spectra show hindered rotation about the N—C=O bond resulting in more than the expected number of lines.

Compound preparation data for other Formula I compounds which are prepared in a manner similar to the above procedures is shown in Tables 3 and 4. The modification of materials to be used in these procedures would be known to one skilled in the art.

TABLE 3

Preparation Data For Formula I Compounds $$R-\underset{\underset{O}{\|}}{\underset{}{C}}-\underset{\underset{CH_3}{|}}{N}-(CH_2)_4-N\diagup\diagdown N-Z \qquad I$$

(BITZ = 1,2-benzisothiazole; TP = Thieno[3,2-c]pyridine; FP = furo[3,2-c]pyridine

| Ex. No. | R | Z | Recryst. Solvent | M.P. °C. | Yield | Formula |
|---|---|---|---|---|---|---|
| 23 | CH₃—CH(CH₃)—CH₂— | BITZ | EtOH—EtOAc 1:1 | 144–145 | 54 | C₂₁H₃₂N₄OS.2HCl |
| 24 | CH₃—CH(CH₃)—CH₂— | FP | MeOH—EtOAc | 227–229 | 48 | C₂₁H₃₂N₄O₂.2HCl.0.6H₂O |
| 25 | CH₃—CH(CH₃)—CH₂— | TP | EtOAc | 132–134 | 47 | C₂₁H₃₂N₄OS.2.4C₇H₈O₃S |
| 26 | CH₃CH₂CH(CH₃)CH₂— | BITZ | EtOAc | 105–107 | 52 | C₂₂H₃₄N₄OS.1.4C₂H₂O₄ |
| 27 | CH₃CH₂—CH=CH—CH₂— (cis) | BITZ | iPrOAc | 92–94 | 15 | C₂₂H₃₂N₄OS.C₂H₂O₄.0.3C₄H₈O₂ |
| 28 | (CH₃)₃CCH₂— | BITZ | EtOAc—CH₃CN | 175–177 | 53 | C₂₂H₃₄N₄OS.HCl.H₂O |
| 29 | (CH₃CH₂)₂CH— | BITZ | iPrOAc | 109–111 | 34 | C₂₂H₃₄N₄OS.1.4HCl |
| 30 | cyclopentyl | BITZ | C₆H₆ | 100–102 | 37 | C₂₂H₃₂N₄OS.HCl |

TABLE 3-continued

Preparation Data For Formula I Compounds

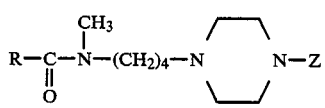

(BITZ = 1,2-benzisothiazole; TP = Thieno[3,2-c]pyridine;
FP = furo[3,2-c]pyridine)

| Ex. No. | R | Z | Recryst. Solvent | M.P. °C. | Yield | Formula |
|---|---|---|---|---|---|---|
| 31 | cyclopentyl | TP | EtOAc | 160–162 | 27 | $C_{22}H_{32}N_4OS \cdot 2C_7H_8O_3S$ |
| 32 | cyclohexyl-$CH_2$ | BITZ | iPrOAc | 169–170 | 42 | $C_{24}H_{36}N_4OS \cdot HCl$ |
| 33 | norbornyl-$CH_2$— | BITZ | EtOAc | 180–181 | 26 | $C_{25}H_{36}N_4OS \cdot HCl$ |

TABLE 4

Preparation Data For Formula I Compounds

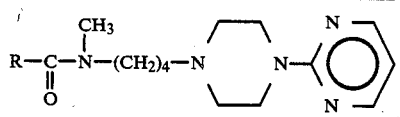

(I: Z = pyrimidinyl)

| Ex. No. | R | Recryst. Solvent | M.P. °C. | Yield | Formula |
|---|---|---|---|---|---|
| 34 | $(H_3C)_2CH$— | EtOAc | 110–112 | 40 | $C_{17}H_{29}N_5O \cdot HCl \cdot 0.5H_2O$ |
| 35 | $(H_3C)_2CH$—$CH_2$— | EtOAc | 120–122 | 47 | $C_{18}H_{31}N_5O \cdot HCl$ |
| 36 | $C_2H_5$—CH($CH_3$)— | EtOAc hexane 1:1 | 125–126 | 54 | $C_{18}H_{31}N_5O \cdot 0.8HCl \cdot 0.6H_2O$ |
| 37 | $(CH_3CH_2)_2CH$— | | 150–152 | — | $C_{19}H_{33}N_5O \cdot HCl$ |
| 38 | $CH_3CH_2$—CH($CH_3$)—$CH_2$— | EtOAc | 102–105 | 59 | $C_{19}H_{33}N_5O \cdot 1.1HCl \cdot 0.6H_2O$ |
| 39 | $(CH_3CH_2CH_2)_2CH$— | EtOAc | 125–126 | 40 | $C_{21}H_{37}N_5O \cdot HCl$ |

TABLE 4-continued
Preparation Data For Formula I Compounds

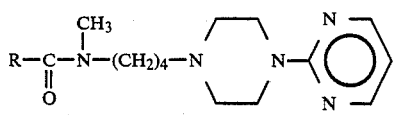

(I: Z = pyrimidinyl)

| Ex. No. | R | Recryst. Solvent | M.P. °C. | Yield | Formula |
|---|---|---|---|---|---|
| 40 | CH₃—C(CH₃)(CH₃)—CH₂— | EtOAc CH₃CN 1:1 | 178–179 | 44 | $C_{19}H_{33}N_5O \cdot HCl$ |
| 41 | cyclopentyl | $C_6H_6$ | 142–144 | 38 | $C_{19}H_{31}N_5O \cdot 1.1HCl \cdot 0.1H_2O$ |
| 42 | cyclohexyl-CH₂ | MeOH—EtOAc 1:1 | 145–149 | 30 | $C_{21}H_{35}N_5O \cdot 1.1HCl \cdot 1.05H_2O$ |
| 43 | bicyclo-CH₂— | MeOH—EtOAc 1:1 | 145–147 | 27 | $C_{22}H_{35}N_5O \cdot 2HCl \cdot H_2O$ |
| 44 | (CH₃)₂C=CH— | EtOAc | 83–86 | 41 | $C_{18}H_{29}N_5O \cdot HCl \cdot H_2O$ |
| 45 | CH₃CH₂(H)C=C(H)—CH₂ | EtOAc | 96–98 | 36 | $C_{19}H_{31}N_5O \cdot 2C_7H_8O_3S \cdot 0.67H_2O$ |

What is claimed is:

1. A compound of Formula I or a pharmaceutically acceptable acid addition salt thereof

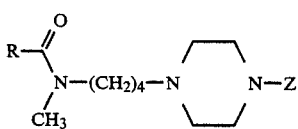

wherein
R is selected from C₄₋₈ alkyl, alkenyl and cycloalkylmethyl, and C₈₋₉ bicyclo hydrocarbon moieties of structure

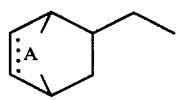

in which A is methylene or ethylene and the full line accompanying the dotted line is a single or double covalent bond; and
Z is a heterocyclic ring system selected from pyrimidin-2-yl, 1,2-benzisothiazol-3-yl, thieno[3,2-c]pyridin-4-yl and furo[3,2-c]pyridin-4-yl.

2. The compound of claim 1 wherein Z is pyrimidin-2-yl.

3. The compound of claim 1 wherein Z is selected from 1,2-benzisothiazol-3-yl, thieno[3,2-c]pyridin-4-yl and furo[3,2-c]pyridin-4-yl.

4. The compound of claim 2, 2,N-dimethyl-N-[4-[4-(2-pyrimidinyl)-1-piperazinyl]butyl]butanamide.

5. The compound of claim 2, 3,3,N-trimethyl-N-[4-[4-(2-pyrimidinyl)-1-piperazinyl]butyl]butanamide.

6. The compound of claim 3, 3,3,N-trimethyl-N-[4-[4-(1,2-benzisothiazol-3-yl)-1-piperazinyl]butyl]butanamide.

7. The compound of claim 2, N-methyl-N-[4-[4-(2-pyrimidinyl)-1-piperazinyl]butyl]cyclopentanecarboxamide.

8. The compound of claim 3, N-[4-[4-(1,2-benzisothiazol-3-yl)-1-piperazinyl]butyl]-N-methylcyclopentanecarboxamide.

9. The compound of claim 3, N,3-dimethyl-N-[4-[4-(1,2-benzisothiazol-3-yl)-1-piperazinyl]butyl]butanamide.

10. The compound of claim 3, N,3-dimethyl-N-[4-[4-(furo[3,2-c]pyridin-4-yl)-1-piperazinyl]butyl]butanamide.

11. The compound of claim 3, N-[4-[4-(1,2-benzisothiazol-3-yl)-1-piperazinyl]butyl-N-methylcyclohexaneacetamide.

12. The compound of claim 2, N-[4-[4-(2-pyrimidinyl)-1-piperazinyl]butyl]-N-methylcyclohexaneacetamide.

13. The compound of claim 3, N,3-dimethyl-N-[4-[4-(thieno[3,2-c]pyridine-4-yl)-piperazinyl]butyl]butanamide.

14. The compound of claim 2, N,3-dimethyl-N-[4-[4-(2-pyrimidinyl)-1-piperazinyl]butyl]butanamide.

15. The compound of claim 3, N-methyl-N-[4-[4-(thieno[3,2-c]pyridin-4-yl)-1-piperazinyl]butyl]cyclopentane.

16. The compound of claim 2, N-methyl-N-[4-[4-(2-pyrimidinyl)-1-piperazinyl]butyl]bicyclo[2.2.1]heptane-2-acetamide.

17. The compound of claim 3, N-[4-[4-(1.2-benzisothiazol-3-yl)-1-piperazinyl]butyl-N-methylbicyclo[2.2.1]heptane-2-acetamide.

18. The compound of claim 3, N-[4-[4-(1.2-benzisothiazol-3-yl)-1-piperazinyl]butyl]-2-ethyl-N-methylbutanamide.

19. The compound of claim 2, 2-ethyl-N-methyl-N-[4-[4-(2-pyrimidinyl)-1-piperazinyl]butyl]butanamide.

20. The compound of claim 2, (E)-N-methyl-N-[4-[4-(2-pyrimidinyl)-1-piperazinyl]butyl]-3-hexenamide.

21. The compound of claim 2, N,2-dimethyl-N-[4-[4-(2-pyrimidinyl)-1-piperazinyl]butyl]propanamide.

22. The compound of claim 2, N-methyl-2-propyl-N-[4-[4-(2-pyrimidinyl)-1-piperazinyl]butyl]pentanamide.

23. The compound of claim 2, N,3-dimethyl-N-[4-[4-(2-pyrimidinyl)-1-piperazinyl]butyl]pentanamide.

24. The compound of claim 2, N,3-dimethyl-N-[4-[4-(2-pyrimidinyl)-1-piperazinyl]butyl]-2-butanamide.

25. The compound of claim 3, N-[4-[4-(1,2-benzisothiazol-3-yl)-1-piperazinyl]butyl]-N,3-dimethyl-pentanamide.

26. The compound of claim 3, N-[4-[4-(1,2-benzisothiazol-3-yl)-1-piperazinyl]butyl]-N-methyl-3-hexenamide.

* * * * *